US00PP35133P2

(12) United States Plant Patent
Snijder

(10) Patent No.: US PP35,133 P2
(45) Date of Patent: Apr. 25, 2023

(54) ***PELARGONIUM* PLANT NAMED 'PEQZ0095'**

(50) Latin Name: ***Pelargonium* interspecific**
Varietal Denomination: PEQZ0095

(71) Applicant: SYNGENTA CROP PROTECTION AG, Basel (CH)

(72) Inventor: Ronald Christiaan Snijder, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/855,899

(22) Filed: Jul. 1, 2022

(51) Int. Cl.
*A01H 5/02* (2018.01)
*A01H 6/42* (2018.01)

(52) U.S. Cl.
USPC ..... Plt./330
CPC ..... *A01H 6/425* (2018.05)

(58) Field of Classification Search
USPC ..... Plt./330
CPC ..... A01H 6/425; A01H 5/02
See application file for complete search history.

*Primary Examiner* — Keith O. Robinson
(74) *Attorney, Agent, or Firm* — Dale Skalla

(57) ABSTRACT

A new *Pelargonium* plant named 'PEQZ0095' particularly distinguished by scarlet red colored inflorescences with large semi-double florets, held above dark green foliage with a zonation, on a vigorous mounding plant.

1 Drawing Sheet

Latin name of the genus and species of the plant claimed: *Pelargonium* interspecific.

Varietal denomination: 'PEQZ0095'.

BACKGROUND OF THE NEW PLANT

The present invention comprises a new *Pelargonium*, botanically known as *Pelargonium* interspecific, and hereinafter referred to by the variety name 'PEQZ0095'.

'PEQZ0095' is a product of a planned breeding program. The new cultivar 'PEQZ0095' has scarlet red colored inflorescences with large semi-double florets, held above dark green foliage with a zonation, on a vigorous mounding plant.

'PEQZ0095' originates from a hybridization in a controlled breeding program made in July 2015, in a greenhouse in Enkhuizen, The Netherlands. The female parent was an unpatented plant of *P.* x *hortorum* parentage identified as 'PEZ-AZ3272-07V' with darker colored florets and a more upright habit when compared to 'PEQZ0095'.

The male parent of 'PEQZ0095' was an unpatented plant of *P.* interspecific parentage, identified as 'Mambo' with lighter green foliage when compared to 'PEQZ0095'. The resultant seed was sown in December 2015.

'PEQZ0095' was selected as one flowering plant within the progeny of the stated cross in May 2016 in a greenhouse in Enkhuizen, The Netherlands.

The first act of asexual reproduction of 'PEQZ0095' was accomplished when vegetative stem cuttings were propagated from the initial selection in June 2016 in a greenhouse in Enkhuizen, the Netherlands.

BRIEF SUMMARY OF INVENTION

Horticultural examination of plants grown from cuttings of the plant initiated in June 2016 in Enkhuizen, The Netherlands and continuing thereafter, has demonstrated that the combination of characteristics as herein disclosed for 'PEQZ0095' are firmly fixed and are retained through successive generations of asexual reproduction.

'PEQZ0095' has not been observed under all possible environmental conditions. The phenotype may vary significantly with variations in environment such as temperature, light intensity, and day length.

A Plant Breeder's Right for this cultivar has not yet been applied for. 'PEQZ0095' has not been made publicly available prior to the effective filing date of this application, notwithstanding any disclosure that may have been made less than one year prior to the effective filing date of this application by the inventor or another who obtained 'PEQZ0095' directly from the inventor.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PEQZ0095' with colors being as true as possible with an illustration of this type.

Figure 1:
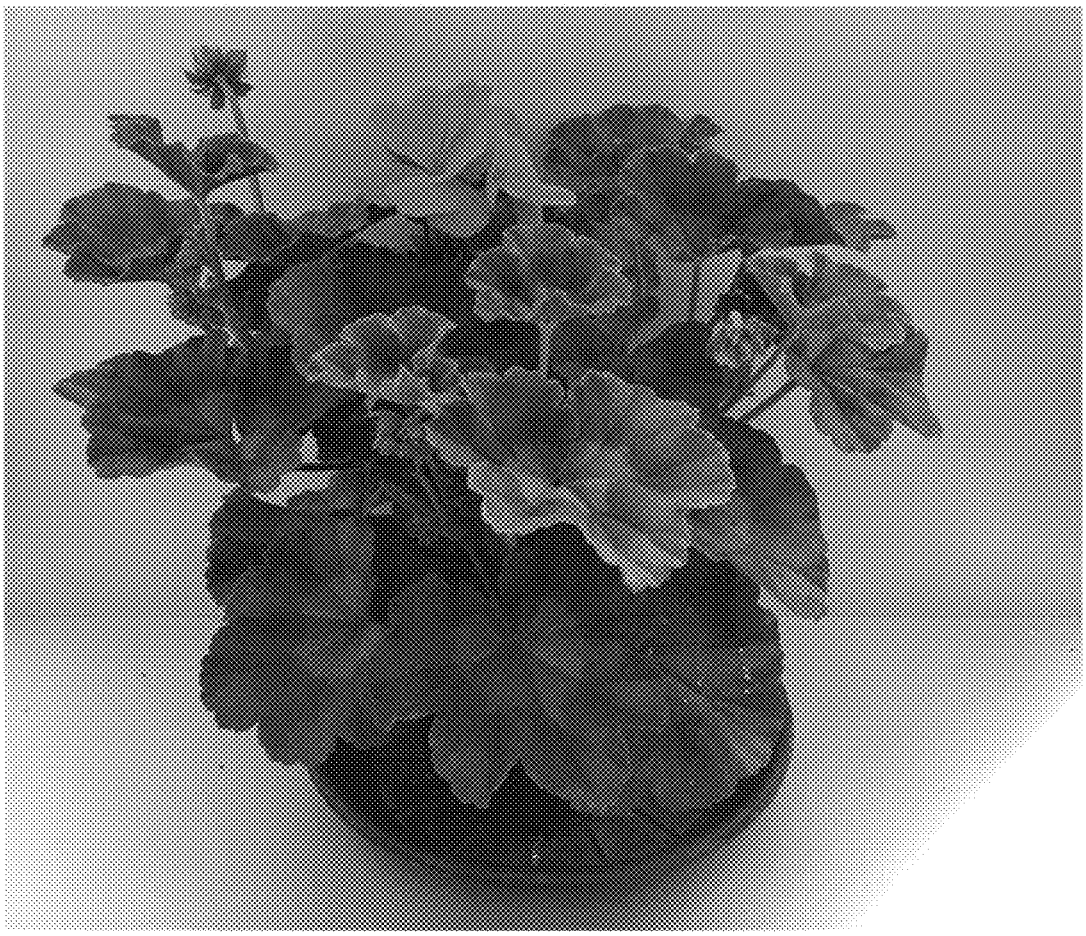
Figure 2:
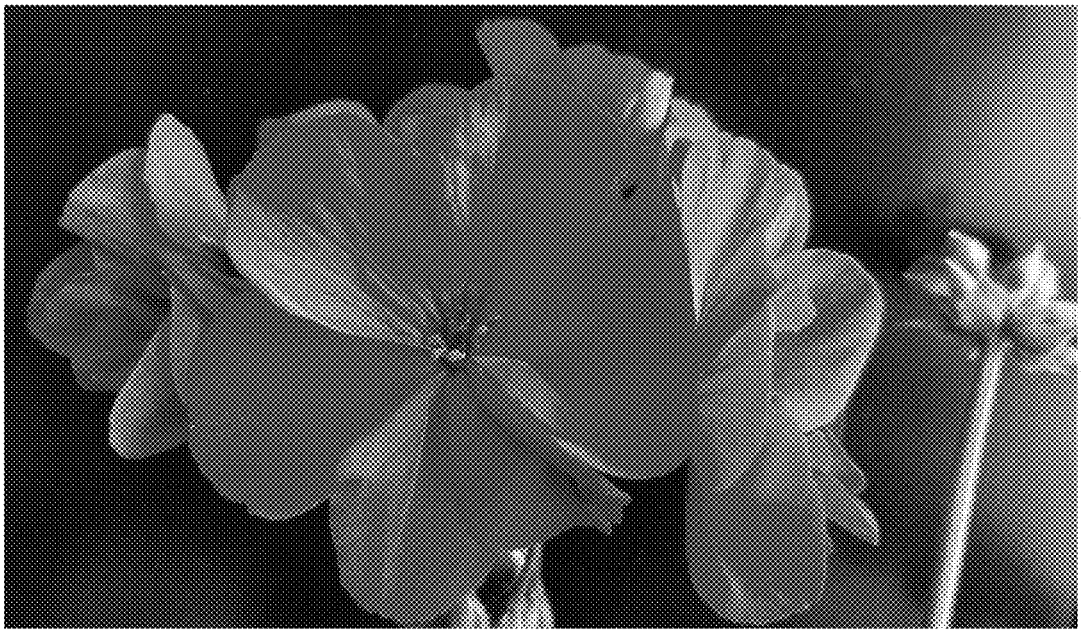

The photographic drawings show in FIG. 1, one flowering plant of the new variety and in FIG. 2, a close-up of an inflorescence.

DETAILED BOTANICAL DESCRIPTION

The plant descriptions and measurements were taken in Enkhuizen, The Netherlands in late June 2022 under natural light. These plants were approximately 18 weeks old and were grown in a 15 cm pots, in a greenhouse trial. The plants shown in the photographs were about 16 weeks old growing in a 12 cm pot in a greenhouse. The photographs were taken in June 2020.

Color references are made to The Royal Horticultural Society Colour Chart (R.H.S.) 2001.

TABLE 1

DIFFERENCES BETWEEN THE NEW VARIETY 'PEQZ0095' AND A MOST SIMILAR VARIETY

| | 'PEQZ0095' | 'Amri Trared' (U.S. Plant Pat. No. 20,245) |
|---|---|---|
| Color upper side upper petal: | Scarlet red, between RHS 43A and RHS 44B | Dark red, RHS 46B |
| Leaf blade color: | Dark green, RHS 137B | Medium green between RHS 144A and 144B |

Plant:

*Form, growth and habit.*—Upright — mounding.
*Plant height.*—30-40 cm.
*Plant height (inflorescence included).*—38-45 cm.
*Plant width.*—33-38 cm.

Roots:

*Number of days to initiate roots.*—15-18 days at about 22 degrees C.
*Number of days to produce a rooted cutting.*—21-23 days at 22 degrees C.
*Type.*—Fine, fibrous, free branching.
*Color.*—RHS N155B but whiter.

Foliage:

*Variegation.*—Absent.
*Immature leaf, color upper surface.*—Closest to RHS 137B.
*Immature leaf, lower surface.*—Closest to RHS 138B.
*Mature leaf, color upper surface.*—Closest to RHS 137A.
*Mature leaf, color lower surface.*—Closest to RHS 138B.
*Length.*—9-12 cm.
*Width.*—11-13 cm.
*Shape.*—Cordate.
*Base shape.*—Cordate.
*Sinus of mature leaf.*—Variable, very narrow to narrow on young mature leaf, more wide on older.
*Leaf base openness.*—Variable, some leaves almost closed, some leaves open or slightly open.
*Apex shape.*—Acute.
*Margin.*—Slightly dentate.
*Texture upper side.*—Hirsute.
*Texture lower side.*—Hirsute.
*Conspicuousness of the zone of the leaf blade.*—Weak.
*Leaf zonation color.*—Between RHS N189A and RHS 187A.
*Color of veins, upper surface.*—RHS 137B, largely indistinct.
*Color of veins, lower surface.*—RHS 144B, becoming indistinct.
*Pattern of veining.*—Palmate.
*Petiole color.*—RHS 143B.
*Petiole length.*—6-9 cm.
*Diameter of petiole.*—0.2 cm.
*Texture.*—Pilose, hirsute, glandular hairs.

Stem:

*Quantity of branches.*—5-9.
*Color of stem.*—Close to RHS 143B.
*Anthocyanin coloration of stem.*—Absent.
*Length of stem.*—18-25 cm.
*Diameter.*—0.6-0.8 cm.
*Length of internodes.*—1-8 cm.
*Texture.*—Sparsely hirsute, pilose, glandular hairs.

Peduncle:

*Color of peduncle.*—From RHS 144A on the base, intensifying up to RHS 187B at the apex.
*Length of peduncle.*—18-23 cm.
*Peduncle diameter.*—0.3 cm.
*Texture.*—Hirsute, glandular hairs.
*Anthocyanin coloration of peduncle.*—A slight anthocyanin coloration is present on the upper half.

Pedicel:

*Color of pedicel.*—RHS 187B.
*Length of pedicel.*—3-3.5 cm.
*Diameter of pedicel.*—0.15-0.2 cm.
*Texture.*—Sparsely pilose, glandular hairs.
*Pedicel swelling.*—Swelling was not observed.

Bud (just before opening):

*Color.*—RHS 46B.
*Length.*—1.5 cm.
*Width.*—0.7 cm.
*Shape.*—Elliptical.

Inflorescence:

*Type.*—Umbel; semi-spherical or nearly semi-spherical.
*Width.*—12-18 cm.
*Lastingness of individual flowers.*—7-9 days at 18° C. temperature.
*Number of inflorescences per plant.*—6-12, with 5-12 immature umbels in various stages.
*Average total number of buds.*—20.5.
*Fragrance.*—None.
*Umbel diameter.*—11-13 cm.
*Umbel depth.*—8-9 cm.

Corolla:

*Form.*—Semi-double.
*Number of petals.*—7-11.
*Diameter of flower.*—5.4-5.8 cm.
*Depth of flower.*—1.5-2 cm.
*Side view shape.*—Concave.
*Color upper petals, upper surface.*—Between RHS 43A and RHS 44B.
*Color upper petals, lower surface.*—RHS 44B, veins fading to RHS 53A.
*Length of upper petals.*—3.2 cm.
*Width of upper petals.*—2.2-2.4 cm.
*Color lower petals, upper surface.*—Between RHS 43A and RHS 44B.
*Color lower petals, lower surface.*—RHS 44B, veins fading to RHS 53B.
*Markings on upper petals.*—Yes, veins RHS 53B at basis, becoming indistinct towards apex.
*Markings on lower petals.*—None.
*Length of lower petals.*—2.5-2.8 cm.
*Width of lower petals.*—2.2-2.4 cm, petaloids smaller and with variable shape.
*Petal shape.*—Obovate to spathulate.
*Apex shape.*—Rounded.
*Margin.*—Entire.
*Base.*—Attenuate.
*Petal texture.*—Papillose on both surfaces.

Calyx:

*Number of sepals.*—5.
*Color of sepals.*—RHS 144B at apex, base RHS 187B.
*Length of sepals.*—1.4-1.6 cm.
*Width of sepals.*—0.2-0.4 cm.
*Sepal shape.*—Lanceolate to linear.
*Apex shape.*—Acute.

*Margins*.—Mostly fused.

*Texture, upper surface*.—Glabrous.

*Lower surface*.—Glandular hairs, hirsute.

*Sepal flexing*.—Mostly unflexed sepals. The narrowest sepals might flex moderately.

Reproductive organs:

Gynoecium:

*Pistil*.—RHS 144D at the base, fading to RHS 187B at the apex.

*Length*.—0.9-1.0 cm.

*Style color*.—RHS 187B.

*Style length*.—0.5 cm.

*Stigma color*.—RHS 187C.

*Ovary color*.—RHS 144D at the base, fading to RHS 187B at the apex.

*Ovary length*.—0.4-0.5 cm.

*Ovary diameter*.—0.2 cm.

Androecium:

*Number of stamens*.—6-9 with 1-5 staminoids.

*Color of filaments*.—RHS N155C at the base, RHS 49B at the apex.

*Length filaments*.—0.8 cm.

*Anther color*.—RHS 51B.

*Length of anthers*.—0.3 cm.

*Color of pollen*.—RHS N169B.

*Pollen amount*.—Ample.

*Fertility/seed set*.—Has not been determined to date.

*Disease/pest resistance*.—Has not been determined to date.

What is claimed is:

1. A new and distinct variety of *Pelargonium* plant named 'PEQZ0095' substantially as illustrated and described herein.

* * * * *